US005672688A

United States Patent [19]

Kobayashi et al.

[11] Patent Number: 5,672,688
[45] Date of Patent: Sep. 30, 1997

[54] IMMUNOGLOBULIN $F_C$ FRAGMENT BOUND TO AN ALKYLATING, ANTIBIOTIC, OR ANTIMETABOLIC ANTITUM OR SUBSTANCE

[75] Inventors: Akira Kobayashi; Takao Ando; Masahiko Fujii, all of Tokyo, Japan

[73] Assignee: Kureha Chemical Industry Co., Ltd., Tokyo, Japan

[21] Appl. No.: 93,885

[22] Filed: Jul. 20, 1993

[30] Foreign Application Priority Data

Jul. 23, 1992 [JP] Japan ................. 4-216650

[51] Int. Cl.⁶ ............... C07K 16/00; C07K 16/18
[52] U.S. Cl. .................. 530/391.7; 530/387.1; 530/391.1; 530/861; 530/866
[58] Field of Search ............... 424/85.8, 178.1, 424/181.1, 809; 530/387.1, 391.7, 391.1, 861, 866

[56] References Cited

U.S. PATENT DOCUMENTS

| 4,867,973 | 9/1989 | Goers et al. ............. 424/85.91 |
| 5,091,523 | 2/1992 | Talebian et al. ........... 536/17.3 |
| 5,200,178 | 4/1993 | Strauss et al. ............ 424/1.1 |

FOREIGN PATENT DOCUMENTS

| A30131836 | 1/1985 | European Pat. Off. . |
| 0314317 | 3/1989 | European Pat. Off. . |
| A20329184 | 8/1989 | European Pat. Off. . |
| A20335476 | 10/1989 | European Pat. Off. . |

OTHER PUBLICATIONS

Capon, D.J. et al., Nature, 337:525–531, 9 Feb. 1989.
Kobayashi, A. et al., J. Bioactive & Compatible Polymers, 3:319–333, Oct. 1988.
Derwent Abstract AN 91-245698.
European Search Report No. EP 93 11 1839.
Perkins, A.C., Eur. J. Nucl Med, 19: 385–386, 1992.
Martin, D.S. et al., Cancer Res, 46: 2189–2192, Apr. 1986.
Waldmann, T.A., Science, 252: 1657–1662, Jun. 21, 1991.
Illustrated Dictionary of Immunology, ed: Cruse & Lewis, 1995, pp. 108–110.
Osband, M.E. et al, Immunology Today, 11(5): 193–195, 1990.

*Primary Examiner*—Susan A. Loring
*Attorney, Agent, or Firm*—Sughrue, Mion, Zinn, Macpeak & Seas

[57] ABSTRACT

A composition comprising as an active ingredient a compound consisting of an immunoglobulin $F_c$ fragment and an alkylating, antibiotic, or antimetabolic antitumor substance bound thereto, and a pharmaceutically acceptable carrier is disclosed. The Fc fragment moiety in the compound is stable in a living body, and thus the activity of the antitumor substance therein is maintained over a long period.

6 Claims, No Drawings

IMMUNOGLOBULIN $F_C$ FRAGMENT BOUND TO AN ALKYLATING, ANTIBIOTIC, OR ANTIMETABOLIC ANTITUM OR SUBSTANCE

BACKGROUND OF THE INVENTION

1. Field of the Invention

The present invention relates to a pharmaceutical composition, particularly an antitumor agent, containing as an active ingredient a compound prepared by binding an antitumor substance to an Fc fragment derived from immunoglobulin.

2. Description of the Related Art

Recently, many antigens related to tumors were found with the advances in immunochemistry. Antibodies which selectively bind to such antigens, i.e., antibodies specific to tumors, were developed. Of these developments, many antitumor agents comprising tumor-specific antibodies and antitumor substances bound thereto were proposed in view of drug delivery systems. Further, an antitumor agent comprising human immunoglobulin (Ig) or F(ab')2 fragment thereof and an antitumor substance bound thereto was described in Japanese Unexamined Patent Publication No. 62-116524.

However, such antitumor agents which are composed of immunoglobulin with an antitumor substance bound thereto and used as the drug delivery system did not prove sufficient effects. The problems were pointed out in such antitumor agents that the inherent activity of the antitumor substance is liable to reduce in the form of a conjugate prepared from immunoglobulin and an antitumor substance, an amount of the conjugate absorbed is decreased because of a large size thereof, and the immunoglobulin fragments F(ab')2 and Fab are not sufficiently stable in a living body. Therefore, there has been a desire for development of an antitumor agent having more superior targeting.

SUMMARY OF THE INVENTION

The present inventors have studied the immunoglobulin, and F(ab')2 and Fab fragments thereof, and thereupon found that, surprisingly, the Fc fragment of immunoglobulin is effective. The present invention is based on this finding.

Accordingly, an object of the present invention is to provide a pharmaceutical composition, particularly an antitumor agent, which can maintain the inherent antitumor activity, and excellent stability of the fragment from immunoglobulin.

Other objects and effects of the present invention will be apparent from the following description.

Therefore, the present invention relates to a pharmaceutical composition containing as an active ingredient a compound prepared by binding an antitumor substance to an Fc fragment derived from immunoglobulin. The compound contained as the active ingredient in the present composition will be referred to hereinafter as the "present active substance".

DESCRIPTION OF THE PREFERRED EMBODIMENTS

The antitumor substance which is the moiety of the present active substance as the active ingredient of the composition according to the present invention may be an alkylating, antibiotic, or antimetabolic antitumor substance. In particular, an antibiotic antitumor substance is preferred.

There may be specifically mentioned mitomycin C, doxorubicin hydrochloride, daunorubicin hydrochloride, bleomycin, actinomycin D, and neocarzinostatin.

The Fc fragment moiety may be derived from any immunoglobulin in any species. The immunoglobulin may be a natural antibody, but does not need to be an antibody specific to tumor. Further, immunoglobulin from any mammals (for example, mouse, rat, rabbit, horse, or bovine), preferably human immunoglobulin, may be used. For example, the Fc fragment may be prepared from immunoglobulin described in biological formulation standards, such as human immunoglobulin, alkylated human immunoglobulin, dried sulfonated human immunoglobulin, dried plasmin-treated human immunoglobulin, dried polyethylene glycol-treated human immunoglobulin, or the like.

The Fc fragment may be prepared from immunoglobulin, for example by the following method. That is, immunoglobulin is digested in an aqueous solution (in particular, a buffer solution) with an enzyme, for example, papain, pepsin, plasmin, or the like, at 20° to 40° C. for 1 to 30 hours. Thereafter, the solution is gel-filtrated to obtain the Fab fragment fraction and Fc fragment fraction. Further, the Fab fragment is removed by a CM-cellulose column or immunoadsorbent. The Fab fragment is obtained from the removed solution. Then, the remaining Fc fragment fraction is collected. Thereafter, the Fc fragment fraction is treated by ammonium sulfate precipitation, dialysis, recrystallization, and other treatment to obtain the purified Fab fragment and Fc fragment.

The present active substance may be prepared by the following method. That is, the antitumor substance is dissolved in an aqueous solvent. As the aqueous solvent, an acidic aqueous solution, an alkaline aqueous solution, a neutral aqueous solution, a phosphate buffer, a sodium borate aqueous solution or the like may be used. To the aqueous solution, a binding agent, for example, carbodiimide, dextran, diethylmalonimidate, isocyanate, or polyglutamic acid, is added, then the Fc fragment derived from immunoglobin is added, and a reaction therebetween is carried out. The reaction temperature is 0° C. to 50° C., preferably 2° to 30° C. The reaction time is 1 minute to 48 hours, preferably 10 minutes to 25 hours. The reaction product is purified by salting out, precipitation, recrystallization, elution, or column separation, or the like to obtain the present active substance. The present active substance contains 1 to 100 µg, preferably 5 to 50 µg, of the antitumor substance in 1 mg of the present active substance, in view of the preparation thereof.

The pharmaceutical composition, in particular the antitumor agent, of the present invention may be administered repeatedly and is effective against various types of human cancers. For example, it is effective against acute leukemia, malignant lymphoma, carcinoma, sarcoma, malignant chorioepithelioma, acute myelogenous leukemia, acute lymphatic leukemia, myeloma, or the like. Any know methods of formulation and administration of conventional antitumor agents may be applied to the pharmaceutical composition of the present invention. The pharmaceutical composition may be administered either orally or parenterally. The pharmaceutical composition may be formulated into either a powder, granules, tablets, capsules, injections, or suppositories. In particular, a tablet or injection is preferable. Aqueous solvents, such as physiological saline solution, sterilized water or Ringer's solution, nonaqueous solvents, isotonizing agents, soothing agents, stabilizers, preservatives, suspending agents, buffer, emulsifiers may be used in injections. For example, 1 g of the present active substance and 5 g of mannitol may be dissolved in distilled water to obtain 50 ml of aqueous solution. The solution is sterilized by an ordinary method, and then divided and poured into injection vials or lyophilized to obtain a stored injection. The stored injection may be diluted with physiological saline solution to obtain the injection when used.

The present active substance may be contained in the formulation in an amount effective to exhibit the antitumor activity, in general 0.01 to 90% by weight, preferably 0.1 to 60% by weight. The dose of the present active substance mainly varies with the state of the disease. However, the dose is 10 to 30,000 mg, preferably 100 to 10,000 mg per once for an adult.

The present active substance maintains the inherent binding activity of the Fc fragment to the Fc receptors of the tumor cells and the inherent antitumor activity of the antitumor substance. Further, the Fc fragment is excellently stable. Therefore, the present active substance, when administered, efficiently reaches the tumor site and resides there for a long period of time, and thus can exhibit antitumor activity over a long period.

EXAMPLE

The present invention now will be further illustrated by, but is by no means limited to, the following examples.

Reference Example (1) Preparation of Human Immunoglobulin

A phosphate buffer saline solution (0.005M-PBS, 100 ml) was added to the serum (1000 ml) from a healthy person, and then a saturated ammonium sulfate aqueous solution (2000 ml; pH7.2) was gradually added while stirring. After the mixture was allowed to stand at 4° C. for 60 minutes, the precipitates were salted out. The precipitates were centrifuged at 8000 rpm for 30 minutes. The resulting precipitates were dissolved in PBS to obtain 1000 ml of the PBS solution. To the PBS solution, a saturated ammonium sulfate aqueous solution (250 ml) was gradually added while stirring. The solution became turbid. The precipitates, if salted out, were removed by centrifugation. To the supernatant, a saturated aqueous solution of ammonium sulfate (250 ml) was added. The mixture was allowed to stand for 60 minutes and then centrifuged at 8000 rpm for 30 minutes. The resulting precipitates were dissolved in PBS (1000 ml). A saturated aqueous solution of ammonium sulfate (500 ml) was added thereto and the mixture was agitated for 60 minutes. The mixture was centrifuged at 8000 rpm for 30 minutes, and then the precipitates were collected. The resulting precipitates were dissolved in PBS (300 ml) and dialyzed. Then, a DEAE-cellulose column (diameter=5 cm; height=50 cm) was used to collect the fraction passing through with a 0.005M phosphate buffer (pH8.0). The passed fraction was dialyzed against distilled water, and then lyophilized to obtain human immunoglobulin (12.5 g; IgG).

(2) Preparation of Human Immunoglobulin Fab and Fc Fragments

Sodium azide (60 mg) was added to a 3% solution (60 ml) of the human immunoglobulin (IgG) obtained in the above (1). The pH was adjusted to 7.5 using a 1N NaOH solution. Plasmin was added so that the concentration thereof reached 4 cu/ml, and then digesting treatment was performed at 35° C. for about 15 hours. After the treatment, the pH was adjusted to 6.5, the mixture was allowed to stand at 4° C. for 1 hour, and then the insoluble contents were removed by centrifugation. The plasmin-digested solution (about 60 ml) was poured into a Sephadex G-200 column for gel filtration to separate the undigested globulin from the digested product (Fab and Fc). Then, the digested product was brought into contact with a CM-cellulose column (pH7.0) to adsorb the Fab and Fc fragments. The column was washed and developed with a 0.01M phosphate buffer (pH7.0) solution containing 0.3M NaCl. Each of the Fab and Fc fragments was collected, respectively, and purified to obtain the desired Fab and Fc fragments.

Example 1

The Fab or Fc fragment derived from human immunoglobulin (IgG), or IgG obtained in the above-mentioned Reference Example was reacted with mitomycin C (MMC) or doxorubicin hydrochloride [adriamycin (ADR)].

That is, human immunoglobulin (IgG; 1.0 g) was dissolved in distilled water (100 ml), and mitomycin C (111.3 mg) was dissolved in the resulting solution. Then, 1-ethyl-3-(3-dimethylaminopropyl)-carbodiimide hydrochloride (262.2 mg) was added at 4° C. therein to react for 24 hours, while the pH was adjusted to 5.5 with a 1.0N HCl aqueous solution. An acetic acid-sodium acetate buffer (pH 5.5; 5 ml) was added to stop the reaction. Then, the reaction mixture was concentrated to 10 ml with an ultrafilter. The concentrated solution (10 ml) was passed through a column packed with Sephadex G-25 (Pharmacia Japan) to completely separate the substances with a high molecular weight and the substances with a low molecular weight from the reaction solution. The eluent containing the substances with a high molecular weight was treated by an ultracentrifugal separation (40,000 g×60 min) and the resulting supernatant was lyophilized at 0° C. to obtain a conjugate of mitomycin C and human immunoglobulin (MMC/IgG). The amount of the mitomycin C bound to the human immunoglobulin (IgG) was measured using 360 nm ultraviolet ray absorption.

The same procedures were repeated, except that the combination of human immunoglobulin (IgG) and mitomycin C was replaced with other combination of mitomycin C (MMC) or adriamycin (ADR) and human immunoglobulin (IgG), the Fab fragment, or the Fc fragment. The results are shown in Table 1. In Tables 1 to 3, the constitutional moieties of the resulting conjugates are abbreviated as follows:

MMC denotes mitomycin C, ADR denotes adriamycin, IgG denotes healthy human immunoglobulin (IgG), Fab denotes the Fab fragment from the above healthy human immunoglobulin (IgG), and Fc denotes the Fc fragment from the above healthy human immunoglobulin (IgG). Further, the binding ratio shows the antitumor substance/immuno moiety.

TABLE 1

| Conjugate (sample) | Reaction time (hr) | Reaction temperature (°C.) | Binding ratio (mg/mg) |
| --- | --- | --- | --- |
| MMC/IgG | 24 | 4 | 0.01/1 |
| MMC/Fab | 24 | 4 | 0.07/1 |
| MMC/Fc  | 24 | 4 | 0.01/1 |
| ADR/Fc  | 24 | 4 | 0.005/1 |
| ADR/IgG | 24 | 4 | 0.004/1 |
| ADR/Fab | 24 | 4 | 0.03/1 |

Example 2

The antitumor activity was measured to determine the effective dose of the present active substance, in accordance with the in vivo method in the first screening method of the National Cancer Institute (NCI).

Tumors (P388/s) were transplanted intraperitoneally in an amount of $10^6/0.1$ ml (physiological saline solution) to CDF/Cry mice (7.5 weeks; female; a group consisting of 6 to 10 mice). After 24 hours and 5 days from the transplantation, the present active substance was dissolved in physiological saline solution and administered intraperitoneally in an amount of 0.1 ml per 10 g of mouse weight. The MST (median survival time) of the test groups was determined (designated as T), and the MST of the control group was determined (designated as C), and then T/C was calculated therefrom. The results are shown in Table 2. The dose to obtain the maximum life-prolonging effect was found from the dose response curve of the adriamycin (ADR) and mitomycin C (MMC) in the present active substance. The maximum life-prolonging effect was obtained with 5.0 mg of ADR and 2.5 mg of MMC in the present active substance per 1 kg of mouse weight.

TABLE 2

| Sample | Dose (mg/kg) | MST | T/C (evaluation) |
|---|---|---|---|
| ADR | Control | 10.6 | |
| | 0.31 | 12.0 | 1.132 (−) |
| | 0.63 | 13.0 | 1.226 (−) |
| | 1.25 | 14.8 | 1.396 (+) |
| | 2.5 | 15.3 | 1.443 (+) |
| | 5.0 | 18.7 | 1.764 (++) |
| | 10.0 | 13.0 | 1.226 (−) |
| MMC | Control | 10.6 | |
| | 0.16 | 12.0 | 1.132 (−) |
| | 0.31 | 13.0 | 1.226 (−) |
| | 0.63 | 15.3 | 1.443 (+) |
| | 1.25 | 18.0 | 1.698 (+) |
| | 2.5 | 25.3 | 2.387 (++) |
| | 5.0 | 16.0 | 1.509 (+) |

Evaluation:
T/C < 1.25 (−)
1.25 to 1.74 (+)
≧ 1.75 (++)

Example 3

The antitumor activities were measured for the various conjugates obtained from Example 1, by repeating the procedure of Example 2, except that the dose of each of the samples was calculated from the amount of ADR or MMC bound so that the amount of ADR in the conjugate became 5 mg per 1 kg mouse weight, and the amount of MMC in the conjugate became 2.5 mg per kg mouse weight, respectively. The results are shown in Table 3.

TABLE 3

| Sample | dose (mg/mg) | MST | T/C (evaluation) |
|---|---|---|---|
| Control (1) | | 10.6 | |
| ADR/IgG | 5*/1250 | 11.1. | 1.047 (−) |
| Control (2) | | 10.1 | |
| ADR/Fab | 5*/1667 | 11.3 | 1.119 (−) |
| ADR/Fc | 5*/1000 | 24.7 | 2.446 (++) |
| Control (3) | | 10.6 | |
| MMC/IgG | 2.5**/250 | 16.7 | 1.575 (+) |
| Control (4) | | 10.1 | |
| MMC/Fab | 2.5**/36 | 16.0 | 1.584 (+) |
| MMC/Fc | 2.5**/250 | >45.0 | >4.455 (++) |
| Com. Ex.*** | | | |
| Control (5) | | 10.6 | |
| IgG | 1250 | 10.8 | 1.019 (−) |
| Fab | 1667 | 11.8 | 1.113 (−) |
| Fc | 1000 | 11.4 | 1.075 (−) |
| ADR | 5 | 18.7 | 1.764 (++) |
| MMC | 2.5 | 25.3 | 2.387 (++) |

* and **: Absolute amounts of ADR and MMC converted from the amount of the conjugate bound.
***: Comparative Examples
Evaluation: T/C < 1.25 (−)
1.25 to 1.74 (+)
≧ 1.75 (++)

Although the present invention has been described with reference to specific embodiments, various changes and modifications obvious to those skilled in the art are deemed to be within the spirit, scope and concept of the present invention.

We claim:

1. A composition comprising a compound consisting of an immunoglobulin $F_c$ fragment and an alkylating, antibiotic, or antimetabolic antitumor or substance bound thereto, and a pharmaceutically acceptable carrier.

2. A composition according to claim 1, wherein the antitumor substance is an alkylating antitumor substance.

3. A composition according to claim 1, wherein the antitumor substance is an antimetabolic antitumor substance.

4. A composition according to claim 1, wherein the antitumor substance is an antibiotic antitumor substance.

5. A composition according to claim 4, wherein the antibiotic antitumor substance is a substance selected from the group consisting of mitomycin C, doxorubicin hydrochloride, daunorubicin hydrochloride, bleomycin, actinomycin D, and neocarzinostatin.

6. A composition according to claim 5, wherein the antibiotic antitumor substance is mitomycin C.

* * * * *